United States Patent

Reddy et al.

[11] Patent Number: 5,560,347
[45] Date of Patent: Oct. 1, 1996

[54] CONDUCTIVE FOAM VAPOR SENSING

[75] Inventors: Sam R. Reddy, West Bloomfield, Mich.; Kalyan P. Gokhale, New Berlin, Wis.

[73] Assignee: General Motors Corporation, Detroit, Mich.

[21] Appl. No.: 395,140

[22] Filed: Feb. 27, 1995

Related U.S. Application Data

[63] Continuation-in-part of Ser. No. 236,071, May 2, 1994.

[51] Int. Cl.$^6$ ..................................... F02M 33/02
[52] U.S. Cl. ..................................... 123/520
[58] Field of Search ..................................... 123/518, 519, 123/520, 198 D; 55/270

[56] References Cited

U.S. PATENT DOCUMENTS

| | | | |
|---|---|---|---|
| 4,663,614 | 5/1987 | Rauchwerger | 340/605 |
| 4,684,382 | 8/1987 | Abu-Isa | 55/316 |
| 5,088,466 | 2/1992 | Tada | 123/520 |
| 5,113,834 | 5/1992 | Aramaki | 123/520 |
| 5,146,902 | 9/1992 | Cook et al. | 123/519 |
| 5,148,793 | 9/1992 | Reddy | 123/520 |
| 5,150,689 | 9/1992 | Yano et al. | 123/519 |
| 5,158,054 | 10/1992 | Otsuka | 123/198 D |
| 5,191,870 | 3/1993 | Cook | 123/520 |
| 5,193,512 | 3/1993 | Steinbrenner et al. | 123/519 |
| 5,203,870 | 4/1993 | Kayanuma et al. | 123/520 |
| 5,215,061 | 6/1993 | Ogawa et al. | 123/520 |
| 5,230,319 | 7/1993 | Otsuka et al. | 123/520 |
| 5,243,944 | 9/1993 | Blumenstock | 123/520 |
| 5,251,592 | 10/1993 | Seki et al. | 123/520 |
| 5,259,353 | 11/1993 | Nakai et al. | 123/520 |
| 5,263,462 | 11/1993 | Reddy | 123/520 |
| 5,297,529 | 3/1994 | Cook et al. | 123/520 |
| 5,299,545 | 4/1994 | Kuroda et al. | 123/520 |
| 5,317,909 | 6/1994 | Yamada et al. | 123/520 |
| 5,339,788 | 8/1994 | Blumenstock et al. | 123/520 |
| 5,353,771 | 10/1994 | Blumenstock et al. | 123/520 |
| 5,383,438 | 1/1995 | Blumenstock | 123/520 |
| 5,429,097 | 7/1995 | Wojts-Saary et al. | 123/520 |

OTHER PUBLICATIONS

"Leak Edge Application Guide/Leak Edge Detection System" –Information of Specific Chemicals, One Plus Corp., 1955 Shermer Rd., Northbrook, IL –Form L9207–2.

*Primary Examiner*—Thomas N. Moulis
*Attorney, Agent, or Firm*—Jeffrey A. Sedlar

[57] ABSTRACT

An apparatus for use in diagnosing an evaporative emission canister collection and purge system. An EVAP system of a vehicle is diagnosed through the use of a mechanism wherein a change in conductivity occurs in response to a change in concentration of fuel vapor in the variably conductive mechanism. By sensing the change in conductivity, a diagnostic mechanism determines whether the vapor collection and purge systems are operating correctly.

14 Claims, 7 Drawing Sheets

CONDUCTIVE FOAM VAPOR SENSING

CROSS REFERENCE TO RELATED APPLICATION

This is a continuation-in-part of commonly assigned patent application Ser. No. 08/236,071, entitled "Conductivity Sensor Diagnostic for Fuel Vapor Handling System," filed May 2, 1994.

BACKGROUND OF THE INVENTION

This invention relates to a fuel vapor handling system. More particularly, the invention is directed to an apparatus and method for use in diagnosing the system.

Automobiles conventionally include a system directed to controlling the emission of fuel vapors generated by the fuel carried in the fuel system. These evaporative emission control systems, known as "EVAP" systems, are implemented as a collateral system to the vehicle's fuel system. The diurnal and running loss vapors they collect result primarily from ambient temperature excursions and the cyclic operation and parking of the vehicle that results from the operator's use of the vehicle as transportation.

An EVAP system typically includes a vapor collection system with an adsorption mechanism to collect and store vapors generated by the fuel system. The EVAP system also includes a purge system to transfer the stored fuel vapors from the adsorbent to the vehicle's engine for consumption in the normal combustion process. The purge system generally includes a normally closed purge valve that selectively opens a passage between the EVAP system and the vehicle's engine to effect a controllable rate of purge.

Conventionally, diagnosis of an EVAP system is generally provided through manual inspection of the system in response to noticeable engine performance degradation or noticeable fuel or vapor leakage. Periodic manual vacuum testing for leaks and purge valve functional checking provides additional effectiveness in diagnosing system operation.

Research has been conducted into developing on-board means for automatically diagnosing EVAP systems, capable of automatically detecting leaks in the system and determining whether the vapor collection and purge systems are operating correctly. Development of on-board automatic diagnostic systems has generally resulted in proposed systems related to mechanisms that close the EVAP system off from the atmosphere and then generate a positive or negative internal system pressure. By then measuring changes in the system pressure, the diagnostic mechanisms attempt to discern whether the evaporative control system is functioning correctly.

Generally, sensitive diagnostic systems are proposed with precision pressure detection devices to work on small pressure differentials. To avoid unacceptable erroneous fault reporting, a pressure based diagnostic system must be able to discern that unexpected pressure gradients are a result of system malfunctions and not changing ambient conditions or other normal collateral effects. This tends to complicate and drive up the cost of a diagnostic mechanism. Accordingly, automatic EVAP diagnostic systems have proven difficult to implement.

Adsorption canister collection and storage system use in on-board refueling vapor recovery (ORVR) systems is known. ORVR systems are vehicle based systems directed at capturing fuel vapors generated by the transfer of fuel from a pump to a vehicle. ORVR systems have been proposed that are configured in a manner similar to an EVAP system including a storage canister and a purge system. Therefore, an automatic system capable of diagnosing an ORVR system is also needed.

SUMMARY OF THE INVENTION

This invention is directed to a diagnostic mechanism for a fuel vapor handling system and generally includes a variably conductive mechanism associated with a fuel vapor storage canister. A sensor to detect the conductivity of the mechanism is provided for use in assisting automatic diagnosis of the system. A diagnostic routine is preferably provided as part of a vehicle's conventional electronic controller, capable of utilizing conductivity data generated from the variably conductive mechanism for diagnosing the system.

The variably conductive mechanism and sensor are used to detect fuel vapor concentration changes caused by fuel vapor flow into the canister and canister purge vapor flow out of the canister for use in diagnosing the system. Optionally, the variably conductive mechanism is either integrated with or located remotely from the canister. Other electrical properties related to conductivity will likewise vary with the varying concentration of fuel vapor and are therefore amenable to providing data for diagnosing the system.

The variable conductivity mechanism is directed to a device that provides for automatically assisting in diagnosis of the system, is capable of functioning without closing the evaporated fuel system off from the atmosphere and can be implemented with minor changes to existing system components.

DETAILED DESCRIPTION OF THE PRESENTLY PREFERRED EMBODIMENT

Figure 1:
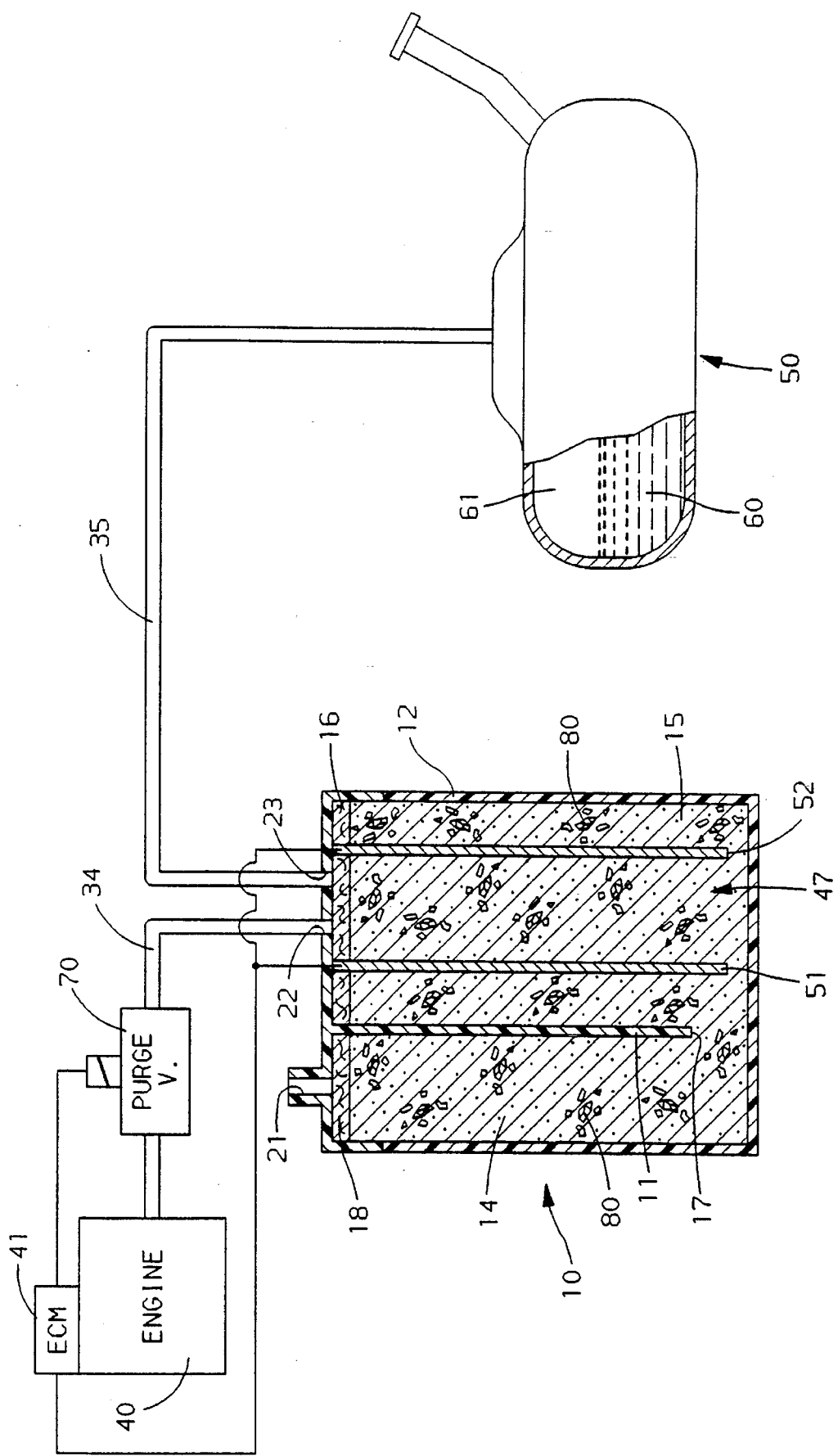
FIG. 1 is a schematic of an EVAP system.

FIG. 1 illustrates an EVAP system of a vehicle's fuel system employing principles of the present invention. The system includes a vapor storage canister 10. Canister 10 exhibits a preferred chambered arrangement created by the exterior wall 12 and the interior wall 11. Chambers 14 and 15 result from this arrangement. Interior wall 11 does not completely separate chamber 14 from chamber 15, rather a passage 17 is established between the chambers. An alternative canister such as a single chambered canister can be used as canister 10.

Wall 12 establishes a substantially closed container by providing a surface on all sides of the canister 10. In the preferred arrangement, wall 12 creates a canister 10, that is substantially rectangular parallelepiped in shape, although the shape is not a critical feature. Selected openings are provided in canister 10 through wall 12. Opening 21 between chamber 14 and the atmosphere functions as a vent. Opening 22, between chamber 15 and conduit 34, functions as a threshold to conduit 34 permitting selected flow out of canister 10. Opening 23, between chamber 15 and conduit 35, functions as a threshold for chamber 15 to conduit 35 permitting flow therebetween.

Conduit 35 establishes a closed flow path between canister 10 and the top of fuel tank 50 that carries a supply of fuel 60. Conduit 34 establishes a closed flow path between canister 10 and an engine 40. Conduit 34 includes purge valve 70 that functions to selectively control the fluid flow rate through conduit 34. Vent opening 21 allows a flow of air into and out of canister 10, thereby facilitating the transfer of fluid into and out of the canister through openings 23 and 22.

Chamber 14 principally contains activated carbon particles 80. Activated carbon is a conventional adsorbent used in EVAP systems. It is preferable to use activated carbon 80 in the present arrangement to provide the required adsorptive characteristics of the mechanism. Chamber 14 contains a screen 18 to prevent the passage of particles from chamber 14 to opening 21 and aid in distributing air flow passing through the vent and into chamber 14. A conventional material used as screen 18 is an polymeric foam, although alternate materials can readily be substituted. Similarly, filter 16 is positioned between chamber 15 and openings 22 and 23.

Chamber 15 also contains activated carbon particles 80 that function as an adsorbent medium. Alternative adsorbent materials may be substituted for the activated carbon. The variably conductive mechanism comprises the adsorbent, activated carbon particles 80.

A sensor 47 is disposed in chamber 15. The sensor illustrated represents a pair of electrodes 51 and 52, between which an electrical current is communicated. Other sensing devices are readily applicable to serving this function. Sensor 47 is used to detect the electrical conductive characteristic of activated carbon 80 in relation to varying concentrations of fuel vapors in the variably conductive mechanism.

The variably conductive mechanism comprised of the adsorbent material 80 that is disposed between electrodes 51 and 52 acts as a variable resistor. The use of activated carbon as the variably conductive mechanism produces an effect wherein an increase in the concentration of fuel vapor results in a corresponding increase in the electrical conductivity properties of the medium and a decrease in fuel concentration results in a corresponding decrease in conductivity. Other variably conductive mechanisms respond in an opposite manner.

Figure 3:
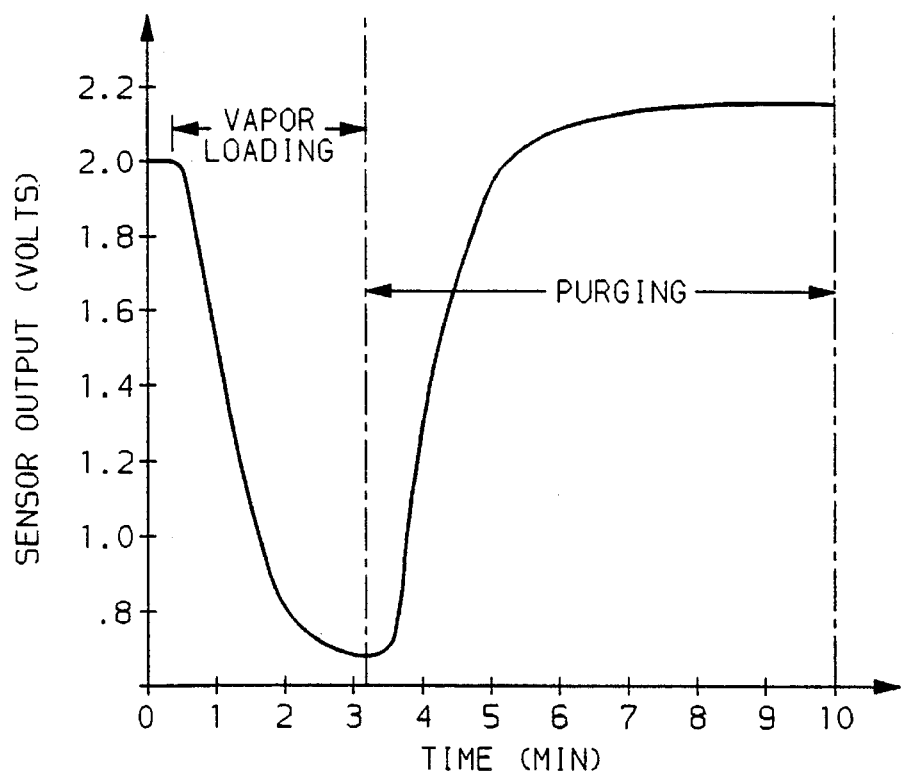
FIG. 3 is a graph of conductivity versus time illustrating a typical canister vapor loading and purge cycle for a selected variably conductive material.

Referring to FIG. 3, a graph demonstrating results of an experimental analysis conducted using a variably conductive mechanism of conventional activated carbon as an adsorbent between two electrodes is illustrated. The vertical axis of the graph indicates voltage values representing a signal from a sensor similar to sensor 47 corresponding to a voltage differential between the two electrodes. The horizontal axis of the graph represents a time component.

FIG. 3 illustrates the effect of a canister vapor loading scenario and a subsequent canister vapor purging scenario. In the present embodiment, an increase in conductivity of the activated carbon 80 results in a reduction in output voltage from sensor 47. This phenomenon is illustrated in the segment of the graph shown in FIG. 3 labeled "vapor loading."

During the segment of the graph representing the vapor loading scenario, an increasing concentration of fuel vapor is accumulating in the activated carbon 80. As the concentration increases, the conductivity increases and there is less of a voltage drop between electrodes 51 and 52. This results in a mechanism that can be used to identify the functional characteristics of the vapor collection system of an EVAP system in the collection of evaporated fuel.

As the concentration of vapor decreases, the voltage drop across the adsorbent between electrodes 51 and 52 increases, indicating a decrease in conductivity. This phenomenon is illustrated in the segment of the graph shown in FIG. 3 labeled "purging." During the purge cycle scenario, vapors are being desorbed or stripped from the adsorbent resulting in a decreasing concentration of fuel vapor in the activated carbon 80. As the concentration decreases, the conductivity decreases and there is a greater voltage drop between electrodes 51 and 52. This results in a mechanism that can be used to identify the functional characteristics of the purge system of an EVAP system.

The electrodes 51 and 52 can be variously configured to achieve particular results. For example, the electrodes can extend through the vertical depth of the canister to predict the extent of canister loading. Since vapors enter the canister through opening 23, the activated carbon 80 will generally become loaded from the top down. Using two electrodes for sensor 47, the extent of canister loading can be predicted from the magnitude of the sensor's output. Using a multiple electrode configuration, the vapor concentration at various levels and throughout the canister can be predicted.

Figure 2:
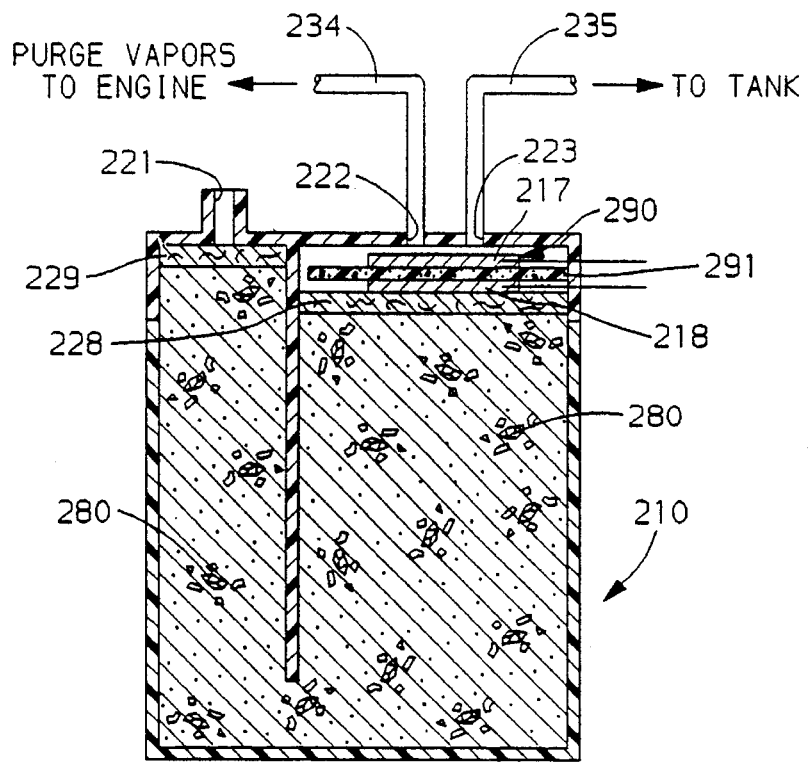
FIG. 2 is a schematic of an alternative embodiment of a canister.

Referring to FIG. 2, an alternative embodiment of the canister according to the invention is illustrated. The operating principles of this embodiment remain substantially the same as those discussed in relation to FIG. 1. The basic diagnostic mechanism relies on the varying conductivity of a material that is subject to varying concentrations of fuel vapors. A sensor is used to read the conductivity at selected occasions for use in diagnosing the system.

Shown in FIG. 2 is canister 210 having a vent opening 221 and openings 222 and 223 that permit flow into and out of the canister 210. The canister contains an adsorbent material 280, preferably comprised of activated carbon. A filter 229 is positioned between the adsorbent 280 and vent 221. Positioned between openings 222 and 223 and the adsorbent 280 is a conductive foam sensor 290 which operates as a variably conductive mechanism. Conductive foam sensor 290 is segregated from the adsorbent 280 by nonconductive foam filter element 228. Optionally, the conductive foam sensor 290 may be located remote from the canister 210, in communication with conduits 234 and 235.

Sensor 290 is comprised of conductive foam material 291 layered between electrodes 217 and 218. The conductive foam is comprised of a polymeric foam such as polyether urethane made conductive by impregnation with carbon, preferably adsorbent type carbon. An example of acceptable materials are FOAMEX SORBACELL and LEWCOTT ACF-F-0.312-T50-150G which are polyether urethane foams made conductive by dipping in a carbon solution.

Figure 4:
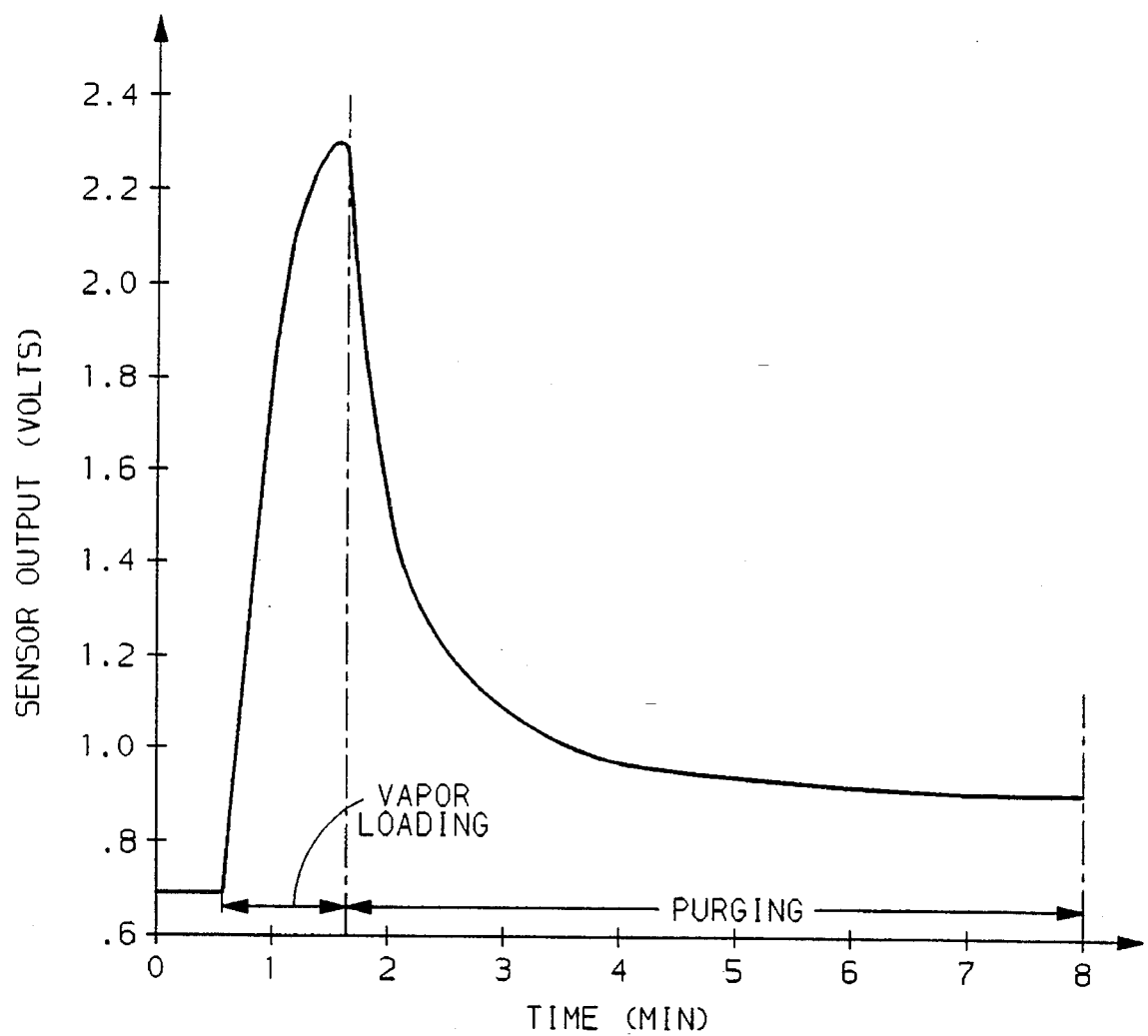
FIG. 4 is a graph of conductivity versus time illustrating a typical canister vapor loading and purge cycle for another selected variably conductive material.

FIG. 4 is a graphical depiction of the variation in conductivity of a conductive foam vapor sensor 290 in response to variations in the concentration of fuel vapors in a canister according to FIG. 3. The graph segment labeled "vapor loading" correspond to a scenario where the purge system is turned off and fuel vapors are accumulating in the adsorbent 280. Notable is the fact that the sensor output voltage increases with the increasing fuel vapor concentration. This phenomenon is indicative of a decrease in conductivity between electrodes 217 and 218, through the foam layer. Therefore, the response of this carbon containing polymeric foam is opposite that of activated carbon when subjected to increases in fuel vapor concentration. This characteristic results in a mechanism that can be used to identify the functional performance of the vapor collection system of an EVAP system and can be utilized in diagnosing the system.

The segment of the graph of FIG. 4 labeled "purging" coincides with a scenario where the purge function is occurring and fuel vapors are being removed from the adsorbent 280. As the concentration of fuel vapors in the canister 210 decreases, the sensor output voltage drops and therefore, conductivity of the conductive foam layer 291 increases. This characteristic results in a mechanism that can be used to identify the functional performance of the purge system of an EVAP system and can be utilized in diagnosing the system.

Figure 5:
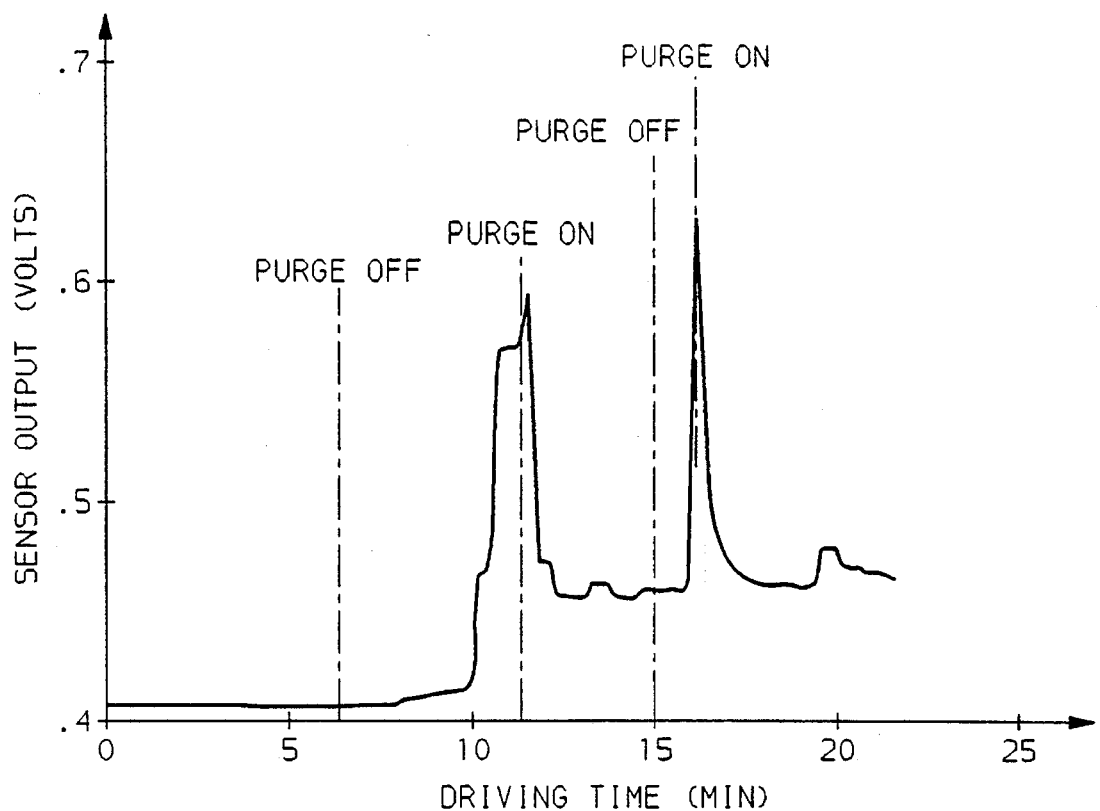
FIG. 5 is a graph of an EVAP system's conductivity sensor output for an in-vehicle operating condition.

FIG. 5 illustrates the continued repeatability of the variably conductive sensing mechanism during the operation of a vehicle containing an EVAP system according to this invention. For the duration of the graph the in-tank fuel temperature (not illustrated), demonstrates a continuously increasing trend as warmed fuel 60 is returned to the fuel tank 50 from the engine 40. Therefore, the quantity of fuel vapor being generated in the system is increasing with time, which effects the sensor output as illustrated by a comparison between the first loading-purge cycle between approximately 10 and 15 minutes, driving time and the second loading-purge cycle between approximately 16 and 21 minutes, driving time. This incremental increase can be predicted to correspond with the increasing tank temperature and is taken into consideration in analyzing conductivity data obtained from the sensor signal when diagnosing a system.

Figure 6:
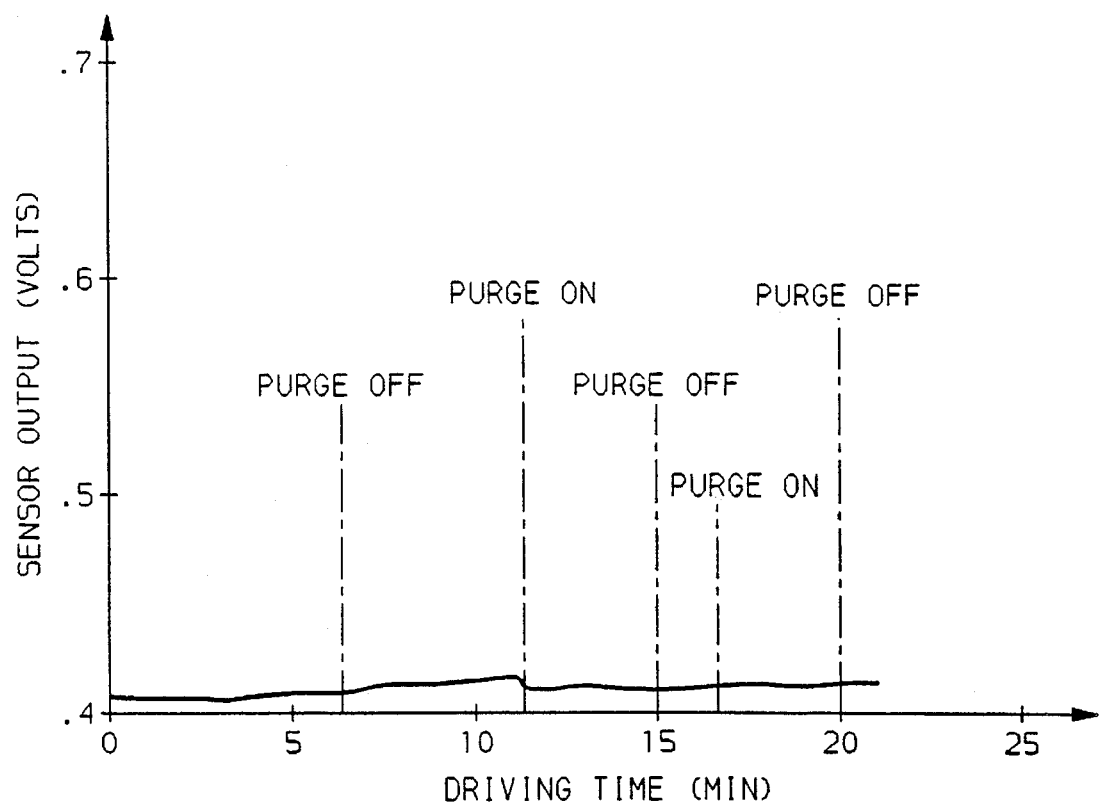
FIG. 6 is a graph of conductivity versus time for the experimental set-up graphed in FIG. 5 with a 0.04 inch diameter opening in the system.

FIG. 6 illustrates the effect a 0.040 inch diameter opening in an EVAP system has on the sensor signal. Although the associated engine 40 is running, returning warmed fuel 60 to the tank 50 and the purge system is cycled on an off, a response showing a marked variation in the conductivity of the mechanism is absent. Certain criteria (identified below), necessary for vapor generation exist for the duration of the graph. Therefore, a variation in conductivity indicative of a correctly functioning vapor loading-purge cycle scenario is predicted to occur and should be shown in FIG. 6. Since the conductivity is not varying as predicted, the conductivity signal data is evaluated and it is determined that a malfunction in the vapor collection or purge system exists.

Referring once again to FIG. 1 the adsorption process will be described. Under certain conditions fuel 60 has the capacity to give off vapor, particularly in response to changing temperatures and pressures, thereby creating a vapor constituent in head space 61 in fuel tank 50. When the vapors cause the pressure inside tank 50 to rise above atmospheric, a flow is generated through conduit 35. Vapors entrained in head space 61 flow through conduit 35 and enter canister 10 through opening 23. The fuel vapors are taken up by activated carbon 80 and the air is allowed to pass to the atmosphere through opening 21. As the concentration of vapor in activated carbon 80 increases the variable conductivity mechanism responds with a change in conductivity.

The conductivity is discerned by the sensor 47 and changes are noted by the associated controls. The change in conductivity is evaluated by comparison to predetermined target values or benchmark values obtained from learning cycles. A successful result from the evaluation, wherein the measured conductivity corresponds to expected values indicates that the EVAP system is working correctly to collect the vapors generated in tank 50.

When the engine 40 is operated, normally closed purge valve 70 is selectively opened to purge fuel vapors from canister 10. When purge valve 70 is open, flow is induced through conduit 34 by engine 40. Air is drawn through vent opening 21 into canister 10 desorbing vapors from activated 80. The purge system operates by entraining the vapors in a flow through opening 22, conduit 34 and into engine 40 for consumption.

As the concentration of vapors in activated carbon 80 decreases, there is a corresponding change in conductivity in the variable conductivity mechanism. The change in conductivity is evaluated by comparison to predetermined target values or benchmark values obtained from learning cycles. A successful result obtained from the evaluation wherein the measured value corresponds to expected values indicates that the EVAP system is working correctly to purge fuel vapors from canister 10.

The information available from sensor 47 is usable in a diagnostic program to evaluate the performance of the EVAP system. Illustrated in FIG. 1, the electronic controls or engine control module (ECM) 41 of a vehicle conventionally receives engine operational data and controls the operation of purge valve 70 accordingly. The ECM 41 takes the form of a digital computer that can be programmed to coordinately run a diagnostic test to evaluate the performance of the EVAP system.

Figure 7:
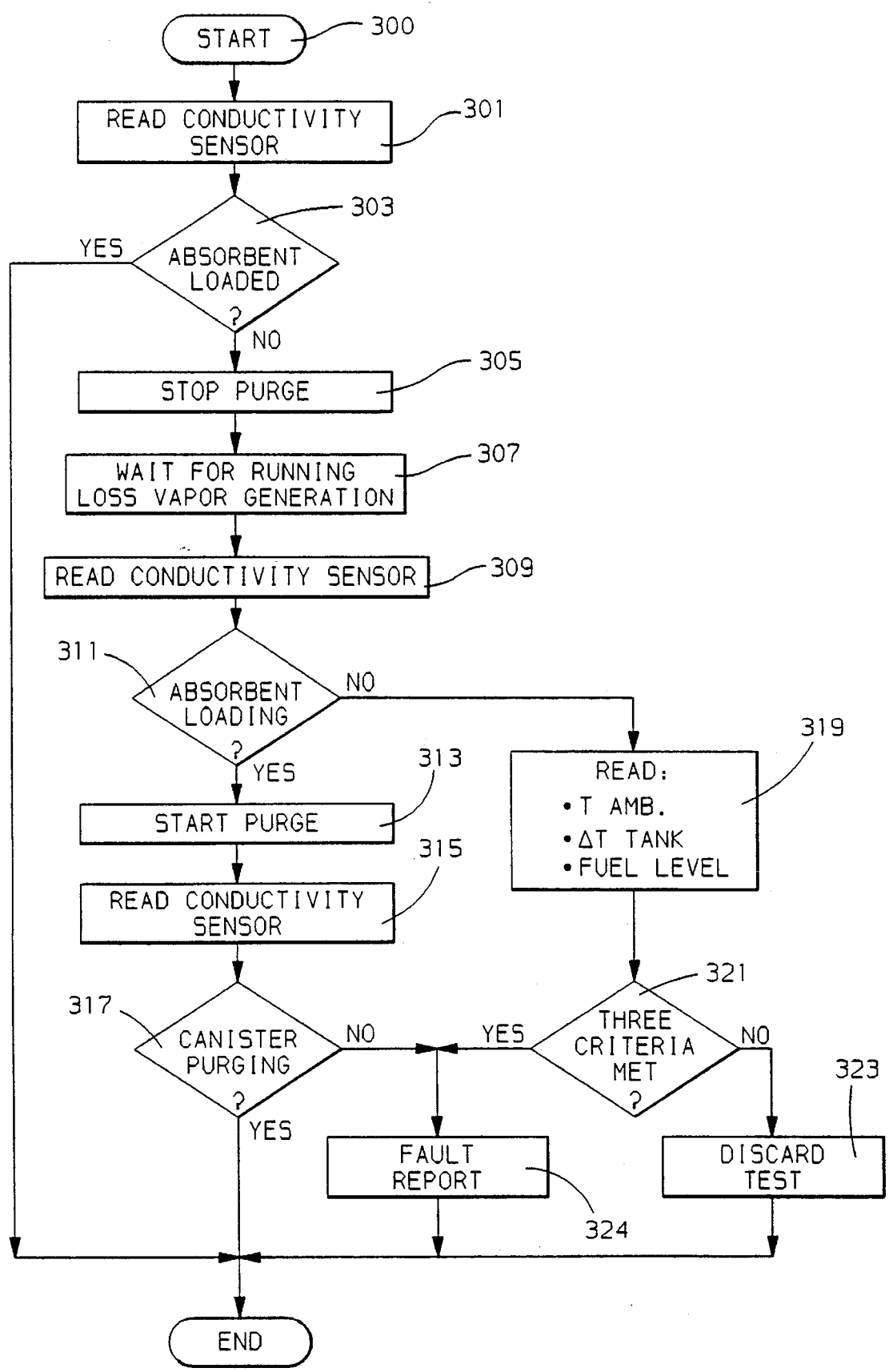
FIG. 7 is a diagram illustrating the steps of a digital control module in diagnosing a fuel vapor handling system.

The diagnostic test occurs during the initial start up routine of engine 40. Referring to FIG. 7, the diagnostic routine is entered at point 300 and proceeds to step 301 where a reading is taken from sensor 47. From step 301 the program proceeds to step 303 where a determination of whether or not the adsorbent bed is loaded with fuel vapor and whether or not the purge function is operating is made.

To determine if the purge function is operating the ECM conducts a memory check of engine operational data, particularly fuel flow calculations which indicate whether collateral fuel flow entered the engine from the EVAP system. A determination that no collateral fuel vapors have been received from the EVAP system is indeterminate and the program continues to step 305. A determination that collateral fuel vapors have been received from the EVAP system is indicative of a correctly operating purge system and a determination of the level of variable conductivity is made to evaluate whether the adsorbent is loaded. A loaded adsorbent condition is indicative of a correctly operating vapor collection system.

If the reading from sensor 47 indicates a conductivity value exists that corresponds to a high concentration of fuel vapor condition, step 303 determines that the adsorbent bed is loaded the vapor collection system is working correctly and the test is complete. If the reading from sensor 47 indicates a conductivity value exists that corresponds to a low concentration of fuel vapor condition, step 303 determines that the adsorbent bed is not loaded and the program proceeds to step 305 where a signal is generated to initiate disabling purge valve 70. When purge valve 70 is disabled, normal purging of canister 10 is prevented.

From step 305 the program proceeds to step 307 where it waits for a specified time t. During time t, the engine 40 must continue to run for the program to proceed. While the engine is running, fuel is being supplied to engine 40 from tank 50 and warmed fuel is being returned from the engine 40 to tank 50. This fuel exchange results in an increase in temperature of fuel 60 in tank 50. In addition, in-tank fuel temperature increases can occur due to underbody air flow that carries air warmed by the engine and exhaust system around the fuel tank and by other collateral sources. The increase in temperature results in running loss vapor generation by fuel 60. The generated vapor, if collected in canister 10, as is expected, causes a change in conductivity to occur in the variable conductivity mechanism.

When specified time t is reached, the program continues from step 307 to step 309. In step 309 a reading is again taken from sensor 47 and the program proceeds to step 311 where a determination of whether the conductivity is increasing or decreasing is made. Since the purge valve 70 has been closed and the engine 40 running, it is predictable when vapor generation will occur. The generated vapor is collected in canister 10 unless a leak in the EVAP or fuel system is allowing it to exit the system to the atmosphere.

At step 311, a determination that the conductivity is changing as predicted corresponds to a correctly functioning vapor collection system of the EVAP system and the program proceeds to step 313 where a signal is generated to initiate starting the purge system. At this point a conventional purge controller operates to selectively open the normally closed purge valve 70 according to engine operational criteria in order to purge fuel vapors from the canister 10.

From step 313, after allowing time for the canister purge function of the EVAP system to take effect, the program proceeds to step 315 where a reading is again taken from sensor 47. From step 315, the program proceeds to step 317 for a determination of whether the conductivity is changing in a manner indicative of a correctly operating purge system. If the purge function of the EVAP system is operating correctly the conductivity will be changing as predicted. If step 317 determines that the reading from sensor 47 is indicative of a correctly operating purge system, the test is complete. If it is determined that the reading is not indicative of a correctly operating purge system, the program proceeds to step 324 and a fault report is generated, completing the test.

From the generation of the fault report, a mechanism such as a warning light on the vehicle's instrument panel is used to indicate to the operator that EVAP system servicing is required. Alternatively, a confirmation test is run at a later time or the next time the vehicle is started before the operator is notified of a diagnostic test failure.

Returning to step 311, if it is determined from the reading of sensor means 47 that the conductivity is not changing as predicted, the program proceeds to step 319. At step 319, a reading is taken of three sensors (not shown), that provide signals indicative of the ambient temperature, the temperature change that has occurred in the fuel tank as a result of engine operation and the fuel level in the fuel tank. For a determination of the fuel temperature change a comparison value corresponding to the fuel temperature when the engine was started is required and therefore, must be available in memory. The comparison value is obtained from a fuel temperature reading preferably taken when the engine is started.

Criterion values are established for the three readings taken at step 319 that represent conditions indicative of whether or not vapor generation is occurring in the fuel system at a level to load the canister. Preferred values for the conditions suitable for use as criteria are: an ambient temperature greater than approximately 60 degrees Fahrenheit, a fuel tank level of less than approximately 60 percent full and an in-tank fuel temperature increase of greater than approximately 5 degrees Fahrenheit. When these criteria are met, vapor generation sufficient to be indicated by the sensor 47 is predicted.

From step 319, the program proceeds to step 321 for an evaluation of whether the three criteria are met. If all of the three criteria are not met, the program proceeds to step 323 and the test is discarded as indeterminate and complete. If all three of the criteria are met, the program proceeds to step 324 where a fault report is generated and the test is complete.

In the foregoing manner, the EVAP system vapor collection system and purge system are diagnosed. The mechanism used in the preferred embodiments described can be readily adapted for use in other fuel vapor handling systems.

Figure 8:
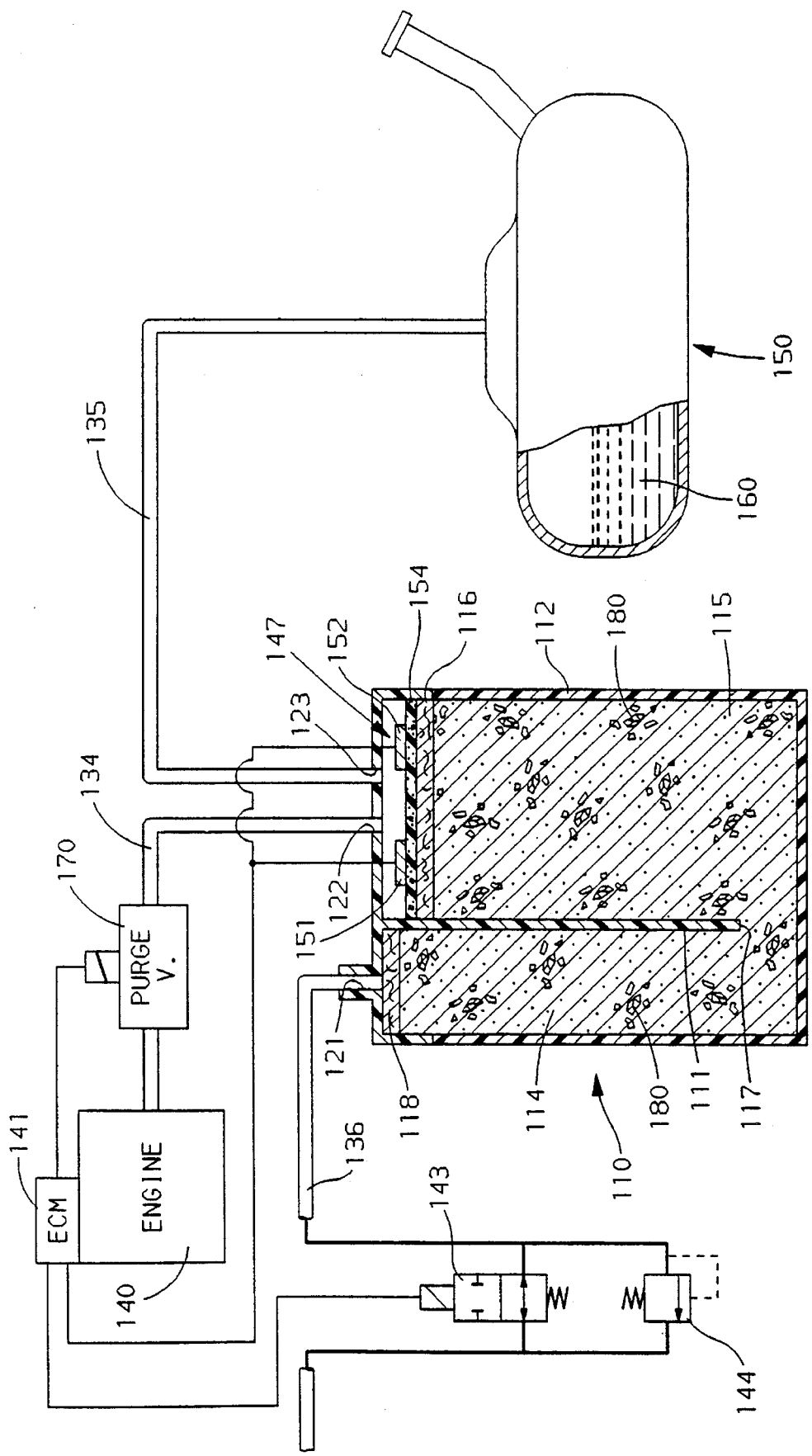
FIG. 8 is a schematic of an alternative EVAP system.

FIG. 8 illustrates an alternative EVAP system of a vehicle's fuel system employing principles of the present invention. The system includes a vapor storage canister 110. Canister 110 exhibits a chambered arrangement created by the exterior wall 112 and the interior wall 111. Chambers 114 and 115 result from this arrangement. Interior wall 111 does not completely separate chamber 114 from chamber 115, rather a passage 117 is established between the chambers. An alternative canister such as a single chambered canister can be used as canister 110.

Wall 112 establishes a substantially closed container by providing a surface on all sides of the canister 110. In the preferred arrangement, wall 112 creates a canister 110, that is substantially rectangular parallelepiped in shape, although the shape is not a critical feature. Selected openings are provided in canister 110 through wall 112. Opening 121 between chamber 114 and conduit 136 functions as a threshold to conduit 136 and operates as a vent. Opening 122, between chamber 115 and conduit 134, functions as a threshold to conduit 134 permitting selected flow out of canister 110. Opening 123, between chamber 115 and conduit 135, functions as a threshold for chamber 115 to conduit 135 permitting flow therebetween.

Conduit 135 establishes a closed flow path between canister 110 and the top of fuel tank 150 that carries a supply of fuel 160. Conduit 134 establishes a closed flow path between canister 110 and an engine 140. Conduit 134 includes purge valve 170 that functions to selectively control the fluid flow rate through conduit 134. Conduit 136 includes normally open solenoid operated vent valve 143 which normally allows a flow of air into and out of canister 110 through conduit 136, thereby facilitating the transfer of fluid into and out of the canister 110 through openings 123 and 122. Vent valve 143 is in communication with ECM 141.

Interconnected with conductor 136 and bypassing vent valve 143 is pressure relief 144. Pressure relief 144 limits the maximum pressure permitted in canister 110 by providing a vent point when solenoid vent valve 143 is closed. Pressure relief 144 comprises a conventionally known relief such as a spring loaded diaphragm pressure relief or an umbrella valve in parallel or integrated with vent valve 143.

Chamber 114 principally contains an adsorbent such as activated carbon particles 180. Activated carbon is a conventional adsorbent used in EVAP systems. Chamber 114 contains a screen 118 to prevent the passage of particles from chamber 114 to opening 121 and aid in distributing air flow passing through the vent and into chamber 114. A conventional material used as screen 118 is a polymeric foam, although alternate materials can readily be substituted. Similarly, filter 116 is positioned between chamber 115 and openings 122 and 123. Chamber 115 also contains activated carbon particles 180 that function as an adsorbent medium.

A sensor 147 is disposed in chamber 115. The sensor illustrated represents a pair of electrodes 151 and 152, between which an electrical current is communicated and conductive foam 154. Other sensing devices are readily applicable to serving this function. Sensor 147 is used to detect the electrical conductive characteristic of conductive foam 154 in relation to varying concentrations of fuel vapors. The sensor 147 is positioned between openings 122 and 123 and the activated carbon 180. Conductive foam 154 is segregated from the activated carbon 180 by nonconductive foam filter element 116.

Electrodes 151 and 152 are positioned in contact with or integrated into conductive foam 154. The conductive foam 154 is comprised of a polymeric foam such as polyether urethane made conductive by impregnation with carbon, preferably adsorbent type carbon. Examples of acceptable materials are FOAMEX SORBACELL and LEWCOTT ACF-F-0.312-T50-150G, which are polyether urethane foams made conductive by dipping in a carbon solution. Preferably, conductive foam 154 comprises polyether urethane foam coated with coconut based activated carbon. As shown in FIG. 8, the conductive foam 154 covers the entire upper cross section of chamber 115 with the electrodes 151 and 152 positioned to measure the conductivity across the top surface of the foam.

Sensor 147 enables the detection of EVAP system leaks as small as 0.02 inches in diameter. Leaks in the tank 150, conduit 135, canister 110 or purge line 134 are detectable. Stage I EVAP system integrity and purge tests are conducted under all conditions and are enabled after every start of engine 140. Stage II diagnostic tests are conducted under certain conditions including when the vapor generation factor (VGF), is greater than 1. Therefore, a two part test as illustrated in FIG. 9 is preferably utilized.

The VGF is a means of expressing the running loss vapor generation which depends on the ambient temperature and the level of fuel 160 in fuel tank 150. VGF=0.0014 (100-%Full)EXP(0.041MAT). Where %Full is the fuel level in fuel tank 150 as a percentage of full and MAT is the manifold air temperature.

Figure 9:
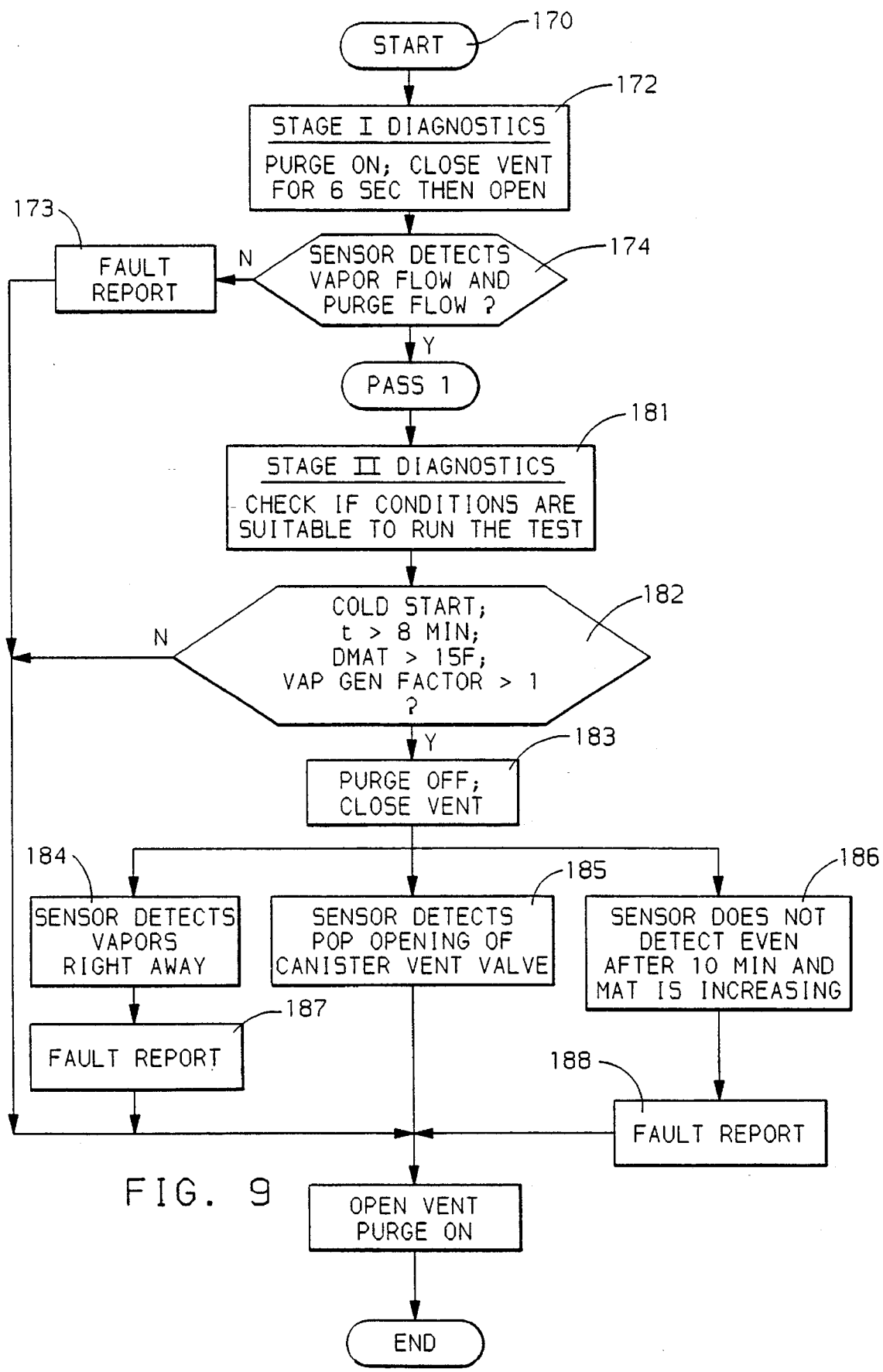
FIG. 9 is a diagram illustrating alternative steps of a digital control module in diagnosing a fuel vapor handling system.

FIG. 9 illustrates a diagnostic test utilized in evaluating the EVAP system of FIG. 8. The diagnostic test occurs during the initial start up routine of engine 140. The test is entered at point 170 and proceeds to step 172 where, with the purge valve 170 open, the vent valve is closed for approximately 6 seconds to draw vapors into the canister 110 and then re-opened to engage vapor purge to the engine 140.

From step 172 the program proceeds to step 174 where ECM 141 evaluates the vapor collection function of the EVAP system by evaluating conductivity changes perceived by sensor 147 in stage I diagnostics. If, at step 172, it is determined that the vapor collection function or purge function are not operating correctly, the program proceeds to 173 where a fault report is generated and the test is complete. If, at step 172, no function irregularities are perceived, the first part of the two-part diagnostic test is complete and the program proceeds to step 181 for a determination of whether to run the second part of the two-part diagnostic test.

At step 181 a delay of approximately eight minutes occurs and the program then proceeds to step 182. After the eight minute delay, DMAT, the change in manifold air temperature since engine start is calculated. Of the conditions necessary for running part two of the test is the requirement that DMAT be greater than approximately fifteen degrees fahrenheit. Additionally, the vapor generation factor must be greater than one. If these conditions are not met, the second part of the test is not conducted and the test is complete. If these conditions are met then conditions are appropriate for conducting the second part of the test and the program proceeds to step 183. The second part of the two-part diagnostic test is capable of perceiving breaches as small as 0.02 inches in diameter anywhere in the system.

At step 183 the vent valve 143 and purge valve 170 are closed to enable system pressurization due to running loss vapor generation. In step 184, an increase in vapor concentration, essentially immediately detected by sensor 147 is indicative of a fault such as a breach in purge line 134 and the program proceeds to step 187 where a fault report is generated and the test is complete. No change in vapor concentration in step 186 as detected by sensor 147, after a period of time such as ten minutes, is indicative of a fault such as a breach in vapor line 135 or fuel tank 150 and the program proceeds to step 188 where a fault report is generated and the test is complete. A delayed increase in vapor concentration in step 185 as detected by sensor 147 is indicative of a correctly operating closed system with an accompanying pop opening of relief valve 144 caused by running loss vapor generation and the test is complete. From steps 185, 188 or 187 the program proceeds to reopen vent valve 143 and purge valve 170 before ending.

In the foregoing manner the EVAP system is diagnosed. System function diagnosis is performed and breaches as small as 0.02 inches in diameter are detectable during appropriate ambient conditions.

Alternatively, a system (not illustrated) configured like the system of FIG. 8 without pressure relief 144 is operable for EVAP system diagnosis. In such a system, stage II of the two-part diagnostic test proceeds by closing vent valve 143 and purge valve 170. This is followed by a timed delay of approximately ten minutes. During the delay, pressure in tank 150 is allowed to build due to running loss vapor generation. Then vent valve 143 is opened to relieve tank pressure. During the venting process, fuel vapors should collect in adsorbent 180. By means of sensor 147, the extent of vapor collection is detected. The extent of vapor collection is indicative of system integrity and operation.

What is claimed is:

1. A vapor handling system comprising:
   a vapor storage container;
   a repeatedly enableable variably conductive vapor sensing mechanism associated with the vapor storage container including a polymeric foam material containing carbon particles having an electrical conductivity related property proportional to a concentration of fuel vapor in the vapor storage container; and
   a vent conduit exiting the vapor storage container and opening to atmosphere including a normally open valve and a relief valve the normally open valve being selectively closable and in combination with the variably conductive vapor sensing mechanism operating in diagnosing the vapor handling system.

2. A vapor handling system according to claim 1 wherein the normally open valve and the relief valve are interconnected in parallel in the vent conduit.

3. A vapor handling system according to claim 2 further comprising a two-part diagnostic test associated with the variably conductive vapor sensing mechanism and the normally open valve.

4. A vapor handling system according to claim 3 further comprising a vapor collection mechanism and a purge mechanism wherein the two-part diagnostic test includes a first part wherein the vapor handling system's vapor collection and purge mechanisms and system integrity are tested and a selectively conducted second part wherein the vapor handling system's integrity is retested.

5. A fuel vapor handling system comprising:
   a fuel vapor storage container;
   an adsorbent in the fuel vapor storage container;
   a repeatedly enableable variably conductive vapor sensing mechanism associated with the fuel vapor storage container including a polymeric foam material containing carbon particles; and
   a vent conduit exiting the fuel vapor storage container and opening to atmosphere including a normally open valve that is selectively closable during a diagnostic routine conducted on the fuel vapor handling system.

6. A fuel vapor handling system comprising:
   a fuel vapor storage container;
   a variably conductive vapor sensing mechanism associated with the fuel vapor storage container including a polymeric foam material containing carbon particles;
   a vent conduit communicating with the fuel vapor storage container and opening to atmosphere including a normally open valve and a relief valve;
   a vapor collection conduit communicating with the fuel vapor storage container;
   a purge conduit communicating with the fuel vapor storage container, wherein vapor is collected in the fuel vapor storage container and purged therefrom through interaction with the vent conduit;
   an automatic and repeatedly enabled test capable of diagnosing the vapor collection and purge functions and the fuel vapor handling system's integrity
   and being capable of a further degree of selectively conducted diagnosis of the integrity of the fuel vapor handling system.

7. A fuel vapor handling system comprising:
   a fuel vapor storage container capable of containing a variable amount of fuel vapor;
   an adsorbent capable of repeatedly adsorbing and desorbing the variable amount of fuel vapor positioned in the fuel vapor storage container;
   a polymeric foam material containing carbon particles positioned in the fuel vapor storage container adjacent the adsorbent and having an electrical conductivity related property continuously and repeatedly variable in proportion to a concentration of the variable amount of fuel vapor in the storage container during adsorption and desorption of the variable amount of fuel vapor; and
   a sensor adjacent to the polymeric foam material to selectively monitor the conductivity related property.

8. A fuel vapor handling system according to claim 7 wherein the polymeric foam material contains coconut based activated carbon particles.

9. A fuel vapor handling system according to claim 7 further comprising a diagnostic system that communicates with the sensor to diagnose the fuel vapor handling system based on the conductivity related property.

10. A fuel vapor handling system according to claim 9 wherein the diagnostic system determines the extent to which the canister is loaded with the variable amount of fuel vapor.

11. An evaporative emission control system for a vehicle operating under variable ambient conditions having an engine and a computer containing engine operational data and a fuel system with a fuel tank containing fuel and having a system with fuel vapor collection and purge functions comprising:
    a fuel vapor storage canister carrying a repeatedly variable concentration of fuel vapor including:
    a polymeric foam material containing coconut based activated carbon particles having a conductivity that repeatedly varies in proportion to the concentration of fuel vapor in the canister;
    a sensor capable of generating a conductivity related signal representative of the concentration of fuel vapor in the canister; and
    a diagnostic system to determine whether the evaporative emission control system is operating to transfer fuel vapor to and from the canister by performing a multiple part diagnostic test including:
    a first stage that is conducted under all ambient conditions and is enabled after every start of the engine and is capable of determining whether the fuel vapor collection and purge functions are operating correctly; and
    a second stage that is conducted under some ambient conditions and is enabled when a sufficient manifold air temperature increase since engine start is detected and when a vapor generation factor, defined as 0.0014 (100-%Full)EXP(0.041MAT), is greater than 1 wherein %Full is a percentage that the fuel tank is full and MAT is the manifold air temperature increase since engine start.

12. A fuel vapor handling system for use in a vehicle having a fuel tank and an engine with a manifold operating under variable ambient conditions comprising:
    a fuel vapor storage container;
    a variably conductive polymeric foam containing carbon particles positioned in the fuel vapor storage container;
    a sensor positioned in contact with the variably conductive polymeric foam;
    a vapor collection conduit communicating with the fuel vapor storage container;
    a purge conduit communicating with the fuel vapor storage container, wherein fuel vapor is collected in the fuel vapor storage container from the vapor collection conduit during a vapor collection function and purged therefrom through the purge conduit during a purge function;
    a vent conduit communicating with the fuel vapor storage container and opening to atmosphere including a selectively closable normally open valve and a pressure relief valve; and
    a diagnostic system communicating with the sensor, the purge valve and the normally open valve including:
    a first stage that is conducted under all ambient conditions and is enabled after every start of the engine and is capable of determining whether the fuel vapor collection and purge functions are operating correctly; and
    a second stage that is conducted under some ambient conditions and is enabled when a sufficient manifold air temperature increase since engine start is detected and when a vapor generation factor, defined as 0.0014 (100-%Full)EXP(0.041MAT), is greater than 1 wherein %Full is a percentage that the fuel tank is full and MAT is the manifold air temperature increase since engine start.

13. A method of diagnosing a fuel vapor handling system having a vapor collection function, a purge function and a vapor storage container with an adsorbent, a repeatedly enableable variably conductive vapor sensing mechanism and a vent conduit opening to atmosphere and being selectively closable by a normally open valve comprising the steps of:

a. closing the normally open valve;
   b. reopening the normally open valve;
   c. reading conductivity of the variably conductive vapor sensing mechanism over a period of time; and
   d. determining whether the reading of the variably conductive vapor sensing mechanism is indicative of a properly operable vapor collection function and a properly operable purge function based on the conductivity of the variably conductive vapor sensing mechanism.

14. A method of diagnosing A fuel vapor handling system of a vehicle having a fuel tank carrying fuel with a manifold conducting air operating under variable ambient conditions and including a fuel vapor storage container; a variably conductive polymeric foam containing carbon particles positioned in the fuel vapor storage container; a sensor positioned in contact with the variably conductive polymeric foam; a vapor collection conduit communicating with the fuel vapor storage container; a purge conduit communicating with the fuel vapor storage container, wherein fuel vapor is collected in the fuel vapor storage container from the vapor collection conduit during a vapor collection function and purged therefrom through the purge conduit during a purge function; and a vent conduit communicating with the fuel vapor storage container including a selectively closable normally open valve and a pressure relief valve comprising the steps of:

a. closing the normally open valve after the engine is started;
   b. waiting a period of time sufficient to draw fuel vapor into the fuel vapor storage container;
   c. opening the normally open valve;
   d. reading the sensor;
   d. determining whether the sensor reading indicates a conductivity indicative of proper operation of the vapor collection and purge functions;
   e. waiting a time sufficient for the air conducted in the manifold to experience an increase in temperature;
   f. determining an actual amount of the increase in temperature;
   g. determining a level of the fuel in the fuel tank;
   h. determining whether the increase in temperature and the level of the fuel are sufficient to enable a second stage test;
   i. when a second stage test is enabled reclosing the normally open valve and determining whether the fuel vapor handling system is securely closed based on the sensed conductivity of the variably conductive vapor sensing mechanism; and
   j. reopening the normally closed valve.

\* \* \* \* \*